US010729491B2

(12) United States Patent
Rioux et al.

(10) Patent No.: US 10,729,491 B2
(45) Date of Patent: Aug. 4, 2020

(54) SYSTEM AND METHOD FOR MARGINAL TISSUE ABLATION

(71) Applicant: Innoblative Designs, Inc., Chicago, IL (US)

(72) Inventors: Robert F. Rioux, Ashland, MA (US); Tyler R. Wanke, Evanston, IL (US); Yearnchee Curtis Wang, Mill Creek, WA (US); Adam Piotrowski, Chicago, IL (US); Tyler Graf, Elm Grove, WI (US); Aldo Ansel, Arlington Heights, IL (US)

(*) Notice: Subject to any disclaimer, the term of this patent is extended or adjusted under 35 U.S.C. 154(b) by 460 days.

(21) Appl. No.: 15/264,244

(22) Filed: Sep. 13, 2016

(65) Prior Publication Data

US 2017/0000559 A1    Jan. 5, 2017

Related U.S. Application Data

(63) Continuation of application No. PCT/US2015/020596, filed on Mar. 13, 2015.
(Continued)

(51) Int. Cl.
*A61B 18/12* (2006.01)
*A61B 18/14* (2006.01)
(Continued)

(52) U.S. Cl.
CPC ...... *A61B 18/1485* (2013.01); *A61B 18/1477* (2013.01); *A61B 18/1815* (2013.01); *A61B 2018/0022* (2013.01); *A61B 2018/00071* (2013.01); *A61B 2018/00077* (2013.01); *A61B 2018/00196* (2013.01);
(Continued)

(58) Field of Classification Search
CPC .......... A61B 2018/00077; A61B 2018/00196; A61B 2018/00214; A61B 2018/0022; A61B 2018/00333; A61B 2018/00505; A61B 2018/00517; A61B 2018/0059;
(Continued)

(56) References Cited

U.S. PATENT DOCUMENTS

| 4,979,948 A | 12/1990 | Geddes et al. |
| 5,562,720 A | 10/1996 | Stern et al. |

(Continued)

FOREIGN PATENT DOCUMENTS

| WO | WO-9404220 A1 | 3/1994 |
| WO | WO-2010099481 A1 | 9/2010 |
| WO | WO-2015142674 A1 | 9/2015 |

OTHER PUBLICATIONS

European Search Report and Search Opinion dated Nov. 13, 2017 for European Patent Application No. EP15765611.7.
(Continued)

*Primary Examiner* — Daniel W Fowler
(74) *Attorney, Agent, or Firm* — Wilson Sonsini Goodrich & Rosati

(57) ABSTRACT

A probe includes a shaft and an applicator head designed to treat irregularly-shaped hollow cavities, such as a cavity in breast tissue created by a lumpectomy procedure. The applicator head has a fixed geometry, and a plurality of electrodes can be advanced from an exterior surface of the applicator head in an omnidirectional pattern. The electrodes are used to deliver radiofrequency current or other energy to ablate the marginal tissue.

21 Claims, 13 Drawing Sheets

Related U.S. Application Data

(60) Provisional application No. 61/953,837, filed on Mar. 14, 2014.

(51) Int. Cl.
*A61B 18/18* (2006.01)
*A61B 18/00* (2006.01)

(52) U.S. Cl.
CPC .............. *A61B 2018/00214* (2013.01); *A61B 2018/00333* (2013.01); *A61B 2018/00505* (2013.01); *A61B 2018/00517* (2013.01); *A61B 2018/00559* (2013.01); *A61B 2018/00577* (2013.01); *A61B 2018/00595* (2013.01); *A61B 2018/1467* (2013.01); *A61B 2018/1861* (2013.01); *A61B 2218/002* (2013.01)

(58) Field of Classification Search
CPC ........... A61B 2018/00577; A61B 2018/00595; A61B 2018/1467; A61B 2018/1861
See application file for complete search history.

(56) References Cited

U.S. PATENT DOCUMENTS

| | | |
|---|---|---|
| 5,713,942 A | 2/1998 | Stern et al. |
| 5,871,483 A | 2/1999 | Jackson et al. |
| 6,123,718 A | 9/2000 | Tu et al. |
| 6,142,993 A | 11/2000 | Whayne et al. |
| 6,258,087 B1 | 7/2001 | Edwards et al. |
| 6,312,429 B1 | 11/2001 | Burbank et al. |
| 6,491,710 B2 | 12/2002 | Satake |
| 6,551,310 B1 | 4/2003 | Ganz et al. |
| 6,638,275 B1 | 10/2003 | McGaffigan et al. |
| 6,978,788 B2 | 12/2005 | Klimberg et al. |
| 7,150,745 B2 | 12/2006 | Stern et al. |
| 7,344,535 B2 | 3/2008 | Stern et al. |
| 7,371,231 B2 | 5/2008 | Rioux et al. |
| 7,556,628 B2 | 7/2009 | Utley et al. |
| 7,632,268 B2 | 12/2009 | Utley et al. |
| 7,769,432 B2 | 8/2010 | Klimberg et al. |
| 7,828,793 B2 | 11/2010 | Thompson et al. |
| 7,942,873 B2 | 5/2011 | Kwan et al. |
| 7,959,631 B2 | 6/2011 | Dicarlo |
| 2001/0031941 A1 | 10/2001 | Edwards et al. |
| 2003/0009165 A1* | 1/2003 | Edwards ............ A61B 18/1206 606/41 |
| 2005/0154386 A1 | 7/2005 | West et al. |
| 2006/0015095 A1* | 1/2006 | Desinger ............ A61B 18/1477 606/41 |
| 2006/0259027 A1 | 11/2006 | Kwan et al. |
| 2007/0083195 A1 | 4/2007 | Werneth et al. |
| 2009/0171340 A1 | 7/2009 | Young |
| 2009/0228001 A1* | 9/2009 | Pacey ................ A61B 18/1477 606/33 |
| 2014/0031810 A1 | 1/2014 | Mahvi et al. |

OTHER PUBLICATIONS

European Search Report dated Nov. 30, 2017 for European Patent Application No. EP15765611.7.
International Search Report and Written Opinion dated Aug. 5, 2015 for International PCT Patent Application No. PCT/US2015/020596.

* cited by examiner

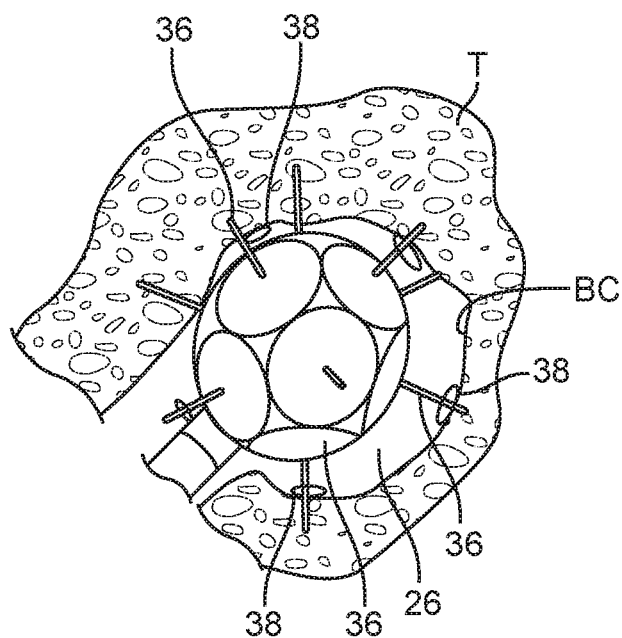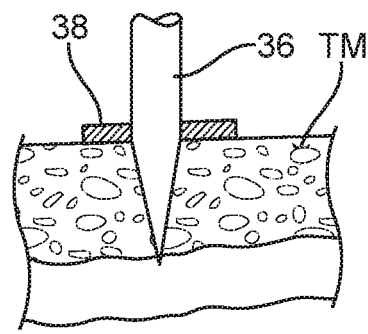
FIG. 8　　　　FIG. 8A
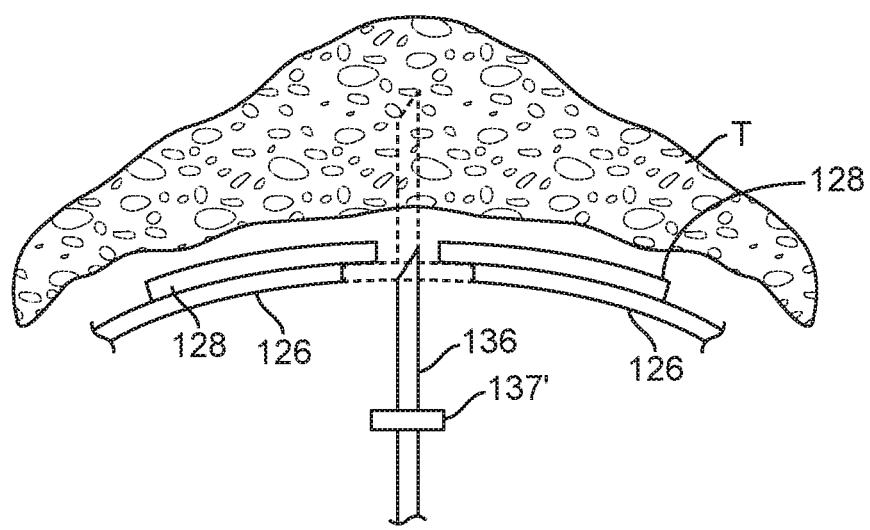
FIG. 8B

Ablation index system (multipolar, bipolar, monopolar); Temperature may be used as well

```
START for each individual electrode circuit.
Ablation indexing system is turned on.
```
↓
Low-power currents are transmitted from electrically- independent subsections of applicator electrodes (such as the tips of the electrode). Only one subsection is actively transmitting at any given time.

↓

Subsections that are not active on the same electrode are acting as current collectors. Only one subsection is collecting current at any given time.

↓

Using a current source and analog-to-digital converter, measure the current and voltage between the current transmitter and collector to obtain the impedance.

↓

Calculate the normalized sum, which scales each impedance depending on which path the current is taking (such as the path from electrode tip to electrode body, electrode tip to applicator head, or electrode tip to dispersive grounding plate).

↓

Compare the normalized impedance and estimated conductivity against the initial calculations. The differential of the two values are used to obtain the ablation index of the tissue between the current transmitter and current collector

↓

Store the normalized impedance, estimated conductivity, transmission configuration, and time.

↓

```
END
Ablation Index Output
```

Side branch:

Temperature data may also be measured and integrated into the ablation index

↓

Estimate the potential conductivity of the tissue under test by using the active current transmitter's surface area.

Ablation Index Algorithm

FIG. 25

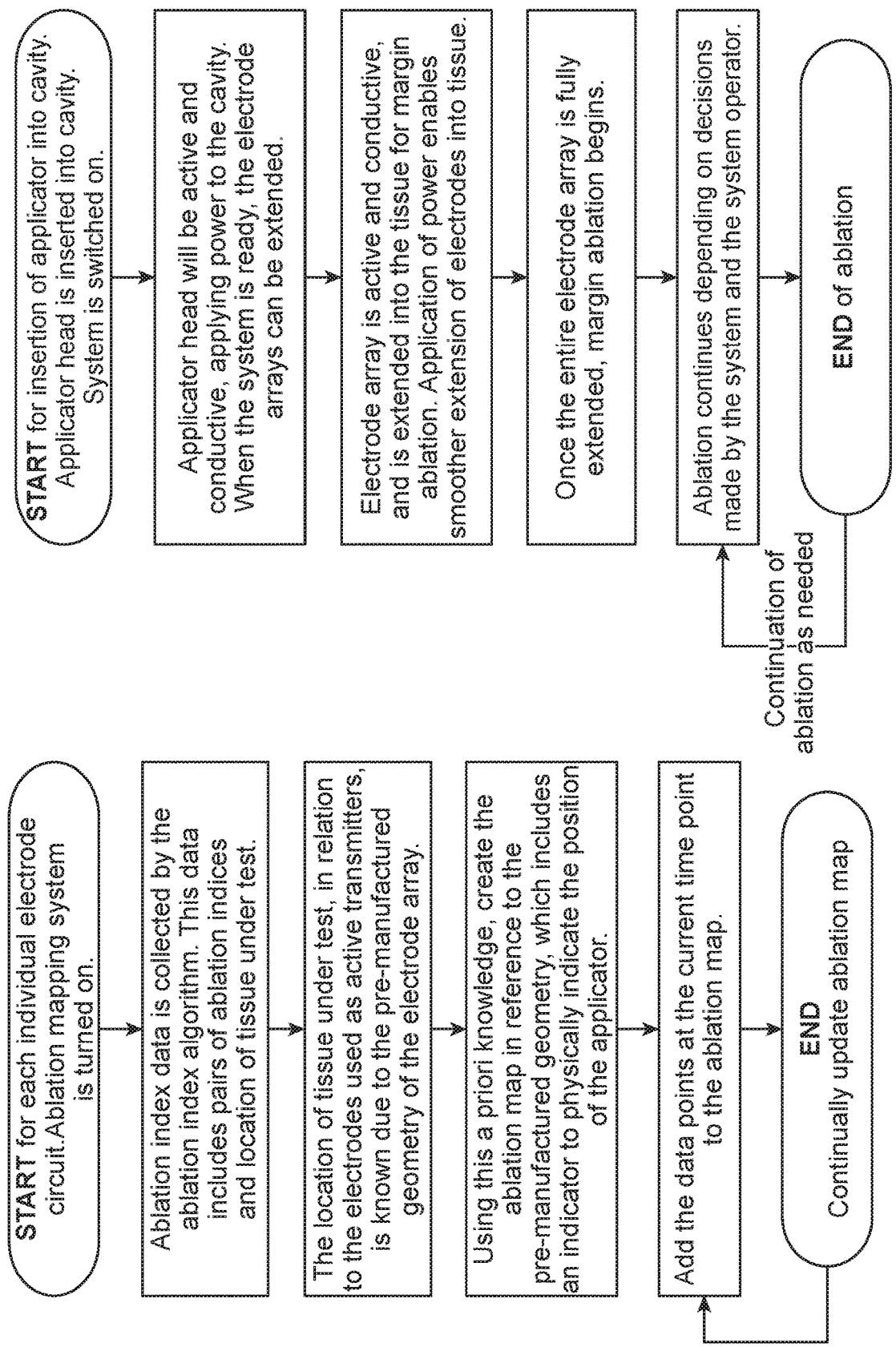

SYSTEM AND METHOD FOR MARGINAL TISSUE ABLATION

CROSS-REFERENCES TO RELATED APPLICATIONS

This application is a continuation of International Patent Application No. PCT/US2015/020596, filed Mar. 13, 2015, which claims the benefit of provisional application no. 61/953,837, filed on Mar. 15, 2014, the full disclosures of which are incorporated herein by reference

BACKGROUND OF THE INVENTION

1. Field of the Invention

The present invention relates generally to medical devices and methods. More particularly, the present invention relates to the structure and use of probes intended to marginally ablate tissue surrounding a tissue cavity.

Treatment of early stage breast cancer typically involves a combination of lumpectomy and whole breast irradiation (WBI). WBI typically utilizes ionizing radiation and can result in short and long-term complications affecting the skin, lungs, and heart. Such risks, when combined with the burden of weeks of daily WBI, drive some women to choose mastectomy instead of lumpectomy and cause up to thirty percent (30%) of women who undergo lumpectomy to stop therapy before completing the full treatment.

One promising alternative to treatment with ionizing radiation is the use of a needle array to deliver radiofrequency energy to the marginal tissue surrounding the cavity left following a lumpectomy. Treatments have been performed with needle arrays intended for treating liver and other solid tissue tumors, and more recently, specialized needle arrays have been proposed for such post-lumpectomy treatments. None of the arrays used or proposed for use thus far have proven to meet all needs and circumstances encountered in when performing marginal cavity tissue ablation.

As such, there remains a need for alternative and improved devices and methods for delivering non-ionizing radiation, such as radiofrequency energy, to deliver precise levels and depths of energy to the tissue immediately surrounding the site of a surgically removed tumor in order to minimize recurrence of the tumor. At least some of these objectives will be met by the inventions described below.

2. Description of the Background Art

US Patent Publication No. 2014/0031810, having common inventors with the present application, describes a probe having an expandable applicator head for radiofrequency ablation of marginal tissue in a tissue cavity. U.S. Pat. No. 6,978,788 describes methods for labeling and ablating a marginal tissue region surrounding a tumor excision site in breast tissue. U.S. Pat. No. 7,942,873 describes an ablation device comprising a needle array and a surrounding sleeve for radiofrequency ablation of marginal tissue in a tissue cavity. Other patents of interest include U.S. Pat. Nos. 4,979,948; 5,562,720; 5,713,942; 5,871,483; 6,123,718; 6,142,993; 6,258,087; 6,491,710; 6,551,310; 7,150,745; 7,344,535; 7,371,231; 7,556,628; 7,632,268; 7,769,432; 7,828,793; and 7,959,631.

BRIEF SUMMARY OF THE INVENTION

The present invention provides a probe having a radiofrequency applicator head specifically designed to treat hollow body cavities, such as irregularly-shaped cavities in breast tissue created by a lumpectomy procedure. The probe structure may be specially adapted and configured to facilitate electrode deployment in a breast or other tissue cavity to allow surgeons to deliver precise, measured doses of radiofrequency energy at controlled depths to the tissue margin surrounding the cavity. Use of the devices and methods of the present invention, however, is not limited to such post-surgical treatments and, as used herein, the phrase "body cavity" includes not surgically created cavities such as this formed by removal of tumors and other tissue lesions but also natural body cavities and passages, such as the ureter (e.g. for prostate treatment), the uterus (e.g. for uterine ablation or fibroid treatment), fallopian tubes (e.g. for sterilization), and the like.

In a first aspect of the present invention, apparatus and systems include probes for ablating a marginal tissue region surrounding a body cavity, such as a cavity in breast tissue following a lumpectomy procedure. The probe comprises a shaft having a distal end. An applicator head is attached at or near the distal end of the shaft and has an outer surface which is fixedly configured to occupy a volume of the body cavity. A plurality of electrodes is disposed within the applicator head and may be reciprocated between a retracted configuration within the applicator head and an advanced configuration where a distal portion of each electrode extends beyond the outer surface of the applicator head. The applicator head may be introduced into the body cavity following a surgery, such as a surgical removal of a malignant tumor, and the electrodes may then be advanced into a marginal region of tissue surrounding the cavity. Energy, typically radiofrequency energy but optionally microwave or other energy that may be delivered by electrodes or electrode-like antennas, is then delivered into the tissue, typically at controlled depths and intensities. By properly spacing and distributing the electrodes over the fixed outer surface of the application head, the energy can be evenly applied throughout the tissue margin and a complete and uniform ablation of the marginal tissue can be achieved, reducing the risk that cancerous cells remain in the marginal tissue after the procedure is complete.

In specific embodiments of the apparatus and systems of the present invention, the shaft is configured as a handle adapted for manual manipulation. In other instances the shaft may be configured for connection to and/or interface with a surgical robot, such as the Da Vinci® surgical robot available from Intuitive Surgical, Inc., Sunnyvale, Calif. In all cases, the shaft may be configured to be held in place by a shape lock or other deployment and suspension system of the type that is anchored to the patient bed and which holds the probe in place while the ablation or other procedure takes place, eliminating the need to a user to manually hold the device for the duration of the treatment. Typically, the applicator head has a plurality of channels, and at least some of the channels reciprocatably receive individual ones of the plurality of electrodes. The applicator head may comprise a solid body having the plurality of channels formed therein. Alternatively, the applicator head may have an open interior and may further comprise a plurality of shaped tubes which define the plurality of channels in the applicator head. Further alternatively, the applicator head may have an open interior and may further comprise a radially expandable support (typically an inflatable bladder) which reciprocatably carries the plurality of electrodes. Still further alternatively, the applicator head may have an open interior where at least some of the individual electrodes are configured to evert around a guide post within the open interior. Aspects of each of these embodiments may be incorporated and combined into a single applicator head.

The electrodes of the probes of the present invention will preferably be configured to advance from the applicator head in an omnidirectional pattern. By "omnidirectional pattern," it is meant that the electrodes will project or radiate radially outwardly from the applicator head, typically from a virtual center of the applicator head, in all directions. It is important that tissue on all sides of the applicator head be treated and ablated, so the electrodes are preferably distributed substantially uniformly over the outer surface of the applicator head. The distances between adjacent electrodes should be substantially equal, preferably varying by no more than 50%, preferably by no more than 25%, and preferably by 10% or less. In the illustrated embodiments, the electrodes usually advance along ray lines from the virtual center, but such orientations are not essential, and individual electrodes may lie along other (non-ray) lines and orientations so long as they are able to penetrate the marginal tissue and are distributed to provide uniform energy delivery over the entire inner surface of the tissue cavity.

In further specific embodiments, the electrodes will be carried within and deflected by channels formed or provided in the applicator head. The channels will typically be arranged to deflect the individual electrodes in the omnidirectional pattern just described, and will typically provide a plurality of paths within the applicator head which radiate radically outwardly from a virtual center point therein. The channels will usually terminate in exit ports distributed substantially over the outer or exterior surface of the applicator head.

In the illustrated embodiments, the electrodes may be configured to advance from the applicator head so that at least some of the electrodes advance in a distally diverging pattern and at least some of the electrodes advance in a proximally diverging pattern. Typically, the electrodes are straight and configured to be advanced in parallel in a distal direction through at least a portion of the shaft. In many embodiments, the electrodes are elastic and configured to be deflected within the applicator head so that some distally diverging electrodes continue to advance distally while said proximally diverging electrodes are everted at an angle between 90° and 180°.

The number and arrangement of electrodes on the applicator head may vary widely. Usually, there will be at least six electrodes, but often there will be 10, 11, 12, 16, 20, 24, or even more. Representative ranges include two to 60, four to 50, six to 36, six to 24, six to 20, and six to 16 electrodes. The electrodes will usually be elongated and will be sufficiently elastic so that they can be bent at angles approaching 180° so that they may de everted to exit the applicator head in a generally proximal direction after being advanced distally through the shaft. Such elastic electrodes will typically be formed from a superelastic metal, such as Nitinol® or a spring stainless steel. Optionally, the elastic electrodes may include coiled or other enhanced elasticity regions to help the electrodes conform the tight bends that may be required. In other embodiments, though, the electrodes may be deployed in alternative fashions that do not require bending, as described below, and may be relatively stiff.

The probes of the present invention may be configured to operate in a monopolar, bipolar, multipolar or other energy delivery protocol. For bipolar or multipolar current delivery, at least some of the electrodes may be configured to be connected to different poles of an associated radiofrequency or other power supply and/or individual electrodes may have two or more isolated electrically conductive regions, where said regions are connectable to different polarities of an associated radiofrequency or other power supply. Often, the plurality of electrodes will comprise at least a first polarity group and a second polarity group. In addition to the electrodes, the probes may have one or more electrodes formed on the shaft and/or disposed on the outer surface of the applicator head.

The applicator head will have a geometry selected to treat the target tissue cavity. For lumpectomy cavities, the applicator head will usually have a spherical, spheroidal or ovoidal outer surface. The number of electrodes advanced from the outer surface will typically be within the ranges set forth above, and the electrodes will preferably be advanced from the applicator head into the marginal tissue region in an omnidirectional pattern, also as described above. The applicator head will typically have diameters or widths in the range from 5 mm to 90 mm, usually from 30 mm to 50 mm for the treatment of lumpectomy cavities. The distal portions of the electrodes will typically extendable beyond the exterior surface of the applicator head by a distance in the range from 0.5 mm to 20 mm, usually from 5 mm to 12 mm for the treatment of lumpectomy cavities. While the electrodes will usually be extendable, the electrodes need not be extended beyond the external surface for use in all circumstances. For example, the electrodes may be energized while still retracted within the interior of the applicator head in order to energize saline or other electrically conductive media which has been released into the body cavity. This may be particularly useful for cauterizing exposed tissue in the cavity before penetration of the electrodes in the tissue for an ablative treatment.

In a second aspect of the present invention, a method for ablating a marginal tissue region surrounding a body cavity comprises introducing an applicator head into the body cavity. The applicator head has a fixed configuration which substantially occupies a volume of the body cavity. A plurality of electrodes are advanced from an outer surface of the applicator head into the marginal tissue region of the body cavity, and energy is delivered through the electrodes to ablate the marginal tissue region. The methods will typically but not necessarily use the ablation probes described above and in the detailed description below.

The methods of the present invention will find their most immediate use in treating tissue at the margins of a tissue cavity remaining after removal of a tumor, such as treating the tissue cavity remaining after a lumpectomy to remove a breast tumor. The methods will be useful for treating other tumors and certain non-malignant conditions, such as lesions and other tissue anamolies in the liver, esophagus, lung, soft tissue (sarcoma), kidney, pancreas, open wounds, and endometrium.

The methods of the present invention may combine other steps and procedure which will enhance or enable the desired marginal ablation. For example, a conductive irrigation fluid may be delivered to a region between the applicator head and the marginal tissue region prior to or concurrently with delivering energy to ablate the tissue region. Delivering the electrically conductive irrigation fluid may comprise infusing the irrigation fluid from the applicator head, for example by infusing the irrigation fluid from a location of at least some of the electrodes, typically through an open interior of the applicator head or through the electrode channels in the applicator head. As a second example, a surface of the marginal tissue region may be cauterized prior to ablating the marginal tissue region, typically by delivering a cauterizing current from the applicator head and/or the electrodes, such as in FIG. 10-12. As a third example, a vacuum may be drawn between the outer surface of the applicator head and a surrounding wall of the body cavity, conveniently be drawing the vacuum is through ports in the outer surface of the applicator head, which may be the electrode delivery ports.

BRIEF DESCRIPTION OF THE DRAWINGS

FIG. 8 illustrates use of an applicator head similar to that illustrated in FIG. 4 having the electrodes of FIGS. 6 and 7 for ablating a tissue cavity.

FIG. 8A illustrates how the penetration-limiting collar limits tissue penetration to control the ablation depth in a tissue margin.

FIG. 8B illustrates a distal end of a single electrode having an electrically conductive disc or flange element dsisposed to engage a surface electrode on the applicator head.

FIG. 25 is a flowchart illustrating an exemplary protocol for determining ablation index.

FIG. 26 is a flowchart illustrating an exemplary protocol for ablation mapping.

FIG. 27 is a flowchart illustrating an exemplary protocol for an exemplary ablation procedure.

DETAILED DESCRIPTION OF THE INVENTION

Figure 1:
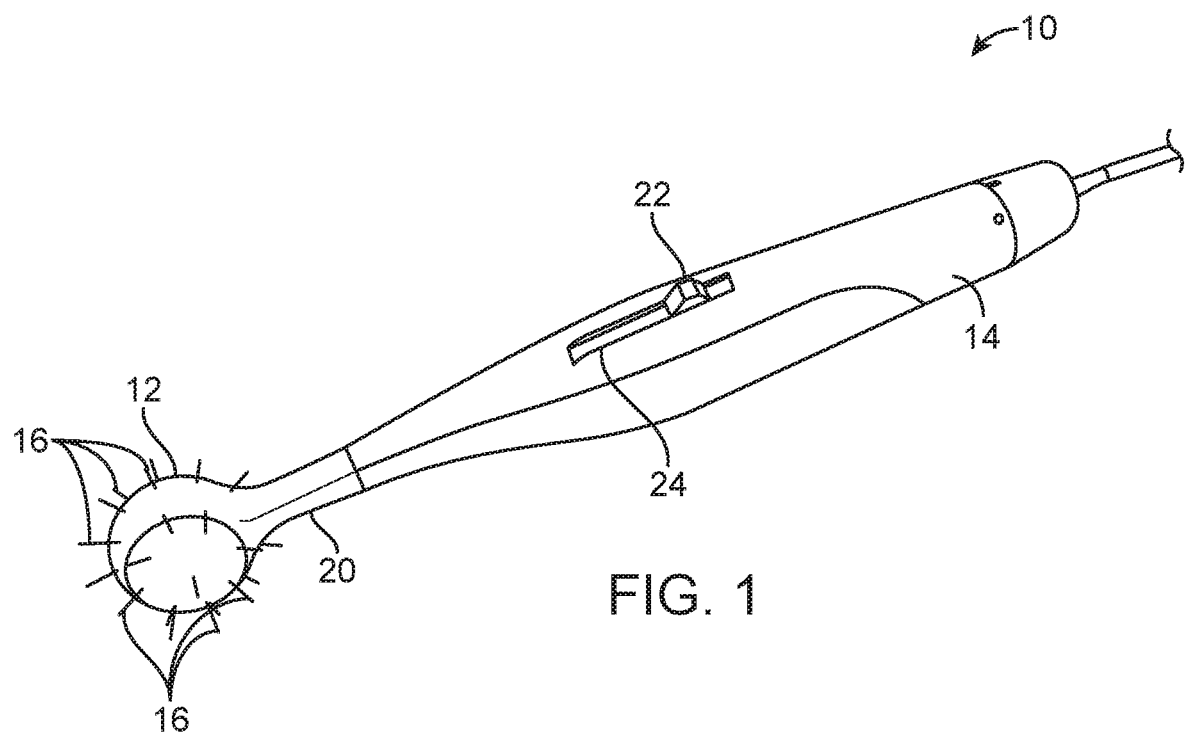
FIG. 1 is a perspective view of a first embodiment of a tissue ablation probe constructed in accordance with the principles of the present invention.
Figure 2:
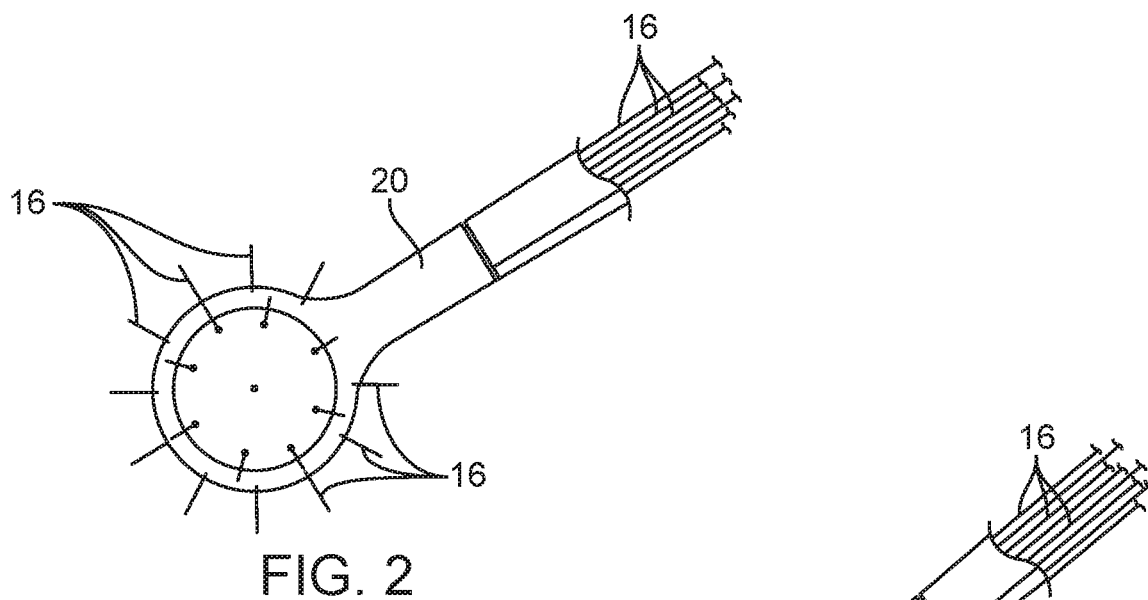
FIG. 2 is an enlarged, detailed view of a distal end of the tissue ablation probe of FIG. 1 shown with a plurality of electrodes extended from an applicator head.
Figure 3:
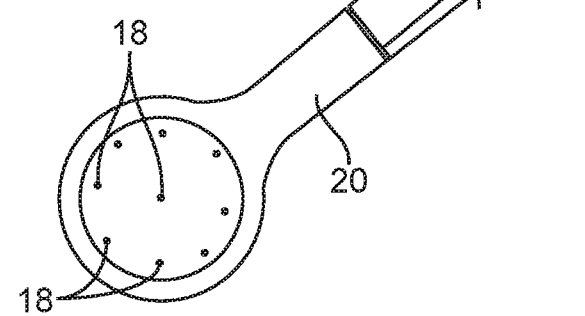
FIG. 3 is view similar to FIG. 2 shown with the electrodes retracted within the applicator head.

An exemplary ablation probe 10 constructed in accordance with the principles of the present invention is illustrated in FIG. 1. The probe 10 includes an applicator head 12 attached or formed at a distal end of a shaft 14 which is typically formed as a handle intended to be manually manipulated by a physician or other user. A plurality of individual electrodes 16 are configured so that they may be extended radially outwardly from the applicator head 10, as shown in FIGS. 1 and 2, or be retracted within the applicator head, as shown in FIG. 3. Usually, the electrodes will be retracted when the applicator head 16 is being introduced into a tissue cavity to be treated, and the electrodes will then be radially advanced when applicator head is properly positioned in order to penetrate the distal ends of the electrodes into the tissue, as illustrated for example in a FIG. 8 discussed below. Each electrode will usually have a tissue-penetrating distal tip, usually being sharpened but optionally relying on the application of a "cutting" current through the electrode as the electrode is advanced into the tissue. Each individual electrodes 16 will typically be reciprocated through a port 18 formed in the applicator head 12, as best seen in FIG. 3. The various internal structures for the applicator head 12 will be described in more detail below with respect to other figures herein.

For the manually manipulated probe embodiments, as shown in FIGS. 1-3, the applicator head 12 will typically be joined to the handle/shaft 14 by a narrow diameter neck region 20. The applicator head 12 will have an enlarged diameter or width, typically being spherical, spheroid, or ovoid or the like, where the enlarged portion is intended to enter and occupy at least a substantial portion of the tissue cavity to be treated. The neck region 20 will usually be disposed within an incision or other entry route through the tissue, thus allowing the tissue to conform around the outer or exterior surface of the applicator head 12, thus helping to assure that the electrodes 16 will be able to penetrate the marginal tissue and uniformly cover all or at least most of the surface area of marginal tissue within the tissue cavity. The tissue probe 10 will usually include a mechanism for advancing and retracting the electrodes 16, such as a slide 22 received in a slot 24 on the handle. The user may advance the slide 22 in order to advance the electrodes. Conversely, the user may retract the slide 22 in a proximal direction in order to retract the electrodes. Specific mechanisms for advancing and retracting the electrodes are described in more detail below.

Figure 20:
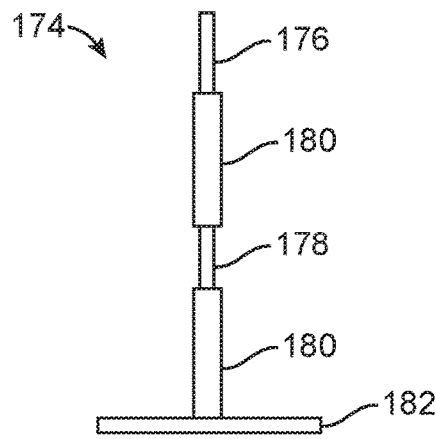
FIGS. 20 and 21 illustrate an exemplary electrode having isolated polarity regions and optionally including a base electrode.
Figure 21:
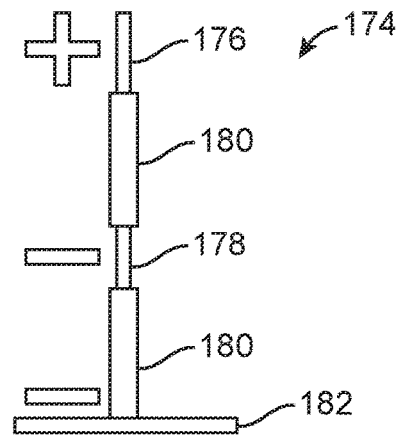
Figure 22:
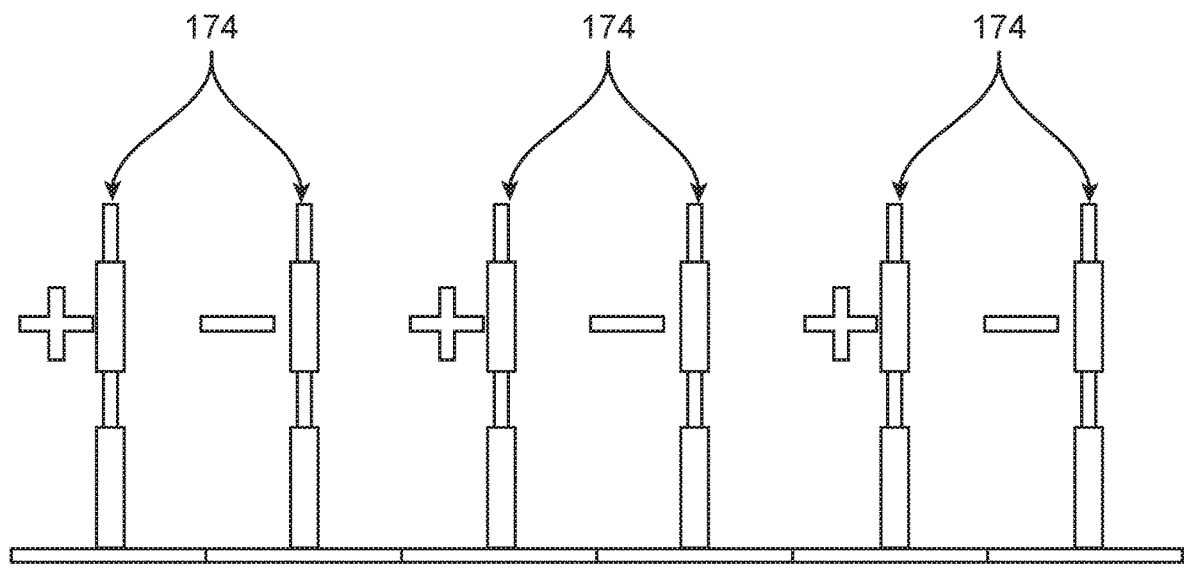
FIG. 22 illustrates a plurality of electrodes which may be arranged in various bipolar patterns.

As illustrated in FIGS. 1-3, the applicator head 12 may be fabricated from polymers and/or other non-electrically conductive materials, such as ceramics, glasses and the like. In this way, only the electrodes 16 will be electrically active. In such cases, the individual electrodes may be powered at a common polarity and the energy applied in a "monopolar" manner, typically using a counter electrode placed on the patient's back or other skin region. Alternatively, individual ones of the electrodes 16 may be powered at different polarities and the energy delivery effected in a bipolar or multi-polar manner Still further, alternatively, the individual electrodes may themselves have isolated electrically conductive regions allowing each electrode to deliver bipolar or multi-polar electrical energy. Specific combinations are illustrated in FIGS. 20-22 below. In alternative embodiments, all or a portion of the applicator head may be fabricated from one or more metals or other electrically conductive materials. In such cases, the head may be electrically coupled to at least some of the electrodes, allowing the head and those electrodes to be powered at a common polarity. In other cases, at least some of the electrodes may be electrically isolated from the electrically conductive applicator head or portions thereof. In those cases, the head and individual electrodes may be powered at different polarities.

Figure 4:
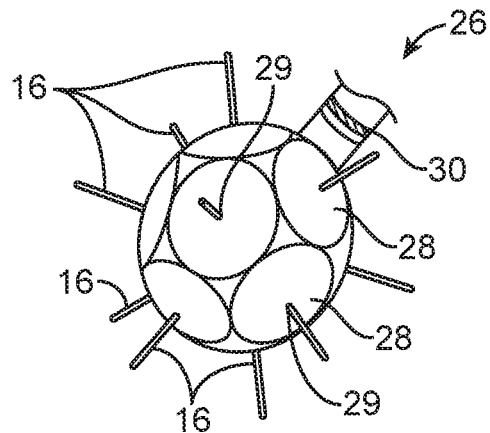
FIG. 4 illustrates an alternative construction of an applicator head useful for the ablation probes of the present invention.

Referring now to FIG. 4, an alternative applicator head 26 is illustrated. Applicator head 26 includes a plurality of surface electrodes 28 formed on an exterior surface of the head. The electrode surfaces 28 are shown to be generally circular, and the electrodes 16 emerged through ports 29 which may be located generally at the center of each circular electrode. The individual surface electrode 28 may be operated at a common polarity or alternatively may be electrically isolated so that they may be powered at difference polarities. Optionally, a ring electrode 30 may be provided on the shaft, typically in the neck region 20 of the shaft. The ring electrode 30 may be powered to extend the ablation region into the incision or tissue path between the cavity and the skin overlying the cavity. The ring electrode 30 may be powered at a common polarity with all other electrodes, or may be powered at a different polarity than at least some of the electrodes in order to effect a bipolar or multi-polar ablation.

Figure 5:
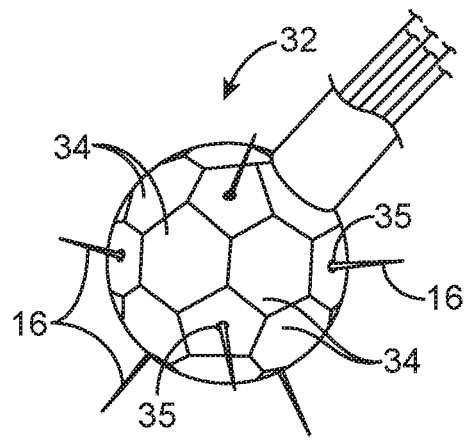
FIG. 5 illustrates a second alternative construction of an applicator head useful for the ablation probes of the present invention.

FIG. 5 illustrates a further embodiment of an applicator head 32 having a polarity of surface electrodes 34. Individual electrodes 16 emerge through ports 35 located near the centers of the hexagonal surface electrodes 34. Use of the hexagonal electrode allows the electrodes to be "closely packed" over the spherical surface of the applicator head 32 so that there are no gaps. The individual surface electrodes 34 may be connected to a common pole of the power supply or to different poles. The surface electrodes 34 may also be powered at the same or different polarities than the individual electrodes 16.

Figure 6:
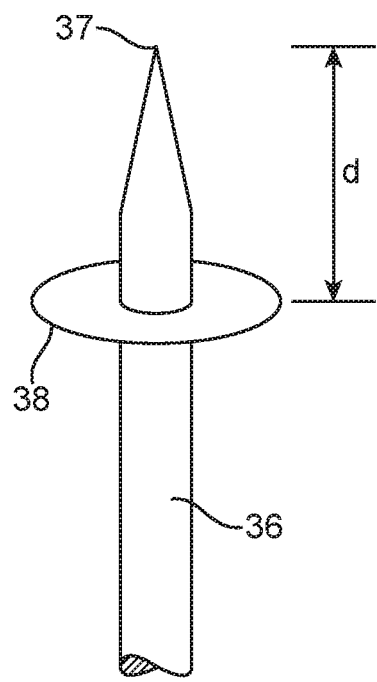
FIG. 6 illustrates a distal end of a single electrode having a penetration-limiting collar.
Figure 7:
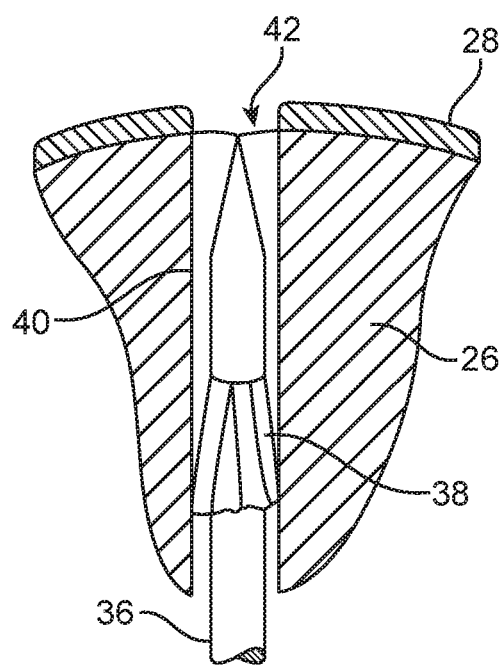
FIG. 7 illustrates the electrode of FIG. 6 with the penetration-limiting collar radially collapsed when constrained in a delivery channel of an applicator head.

Referring now FIGS. 6 and 7, the individual electrodes may take a variety of forms. Most simply, the electrodes may be elongate, elastic electrically conductive metal elements or rods which can be advanced through the shaft to emerge radially outwardly from the applicator head, as shown in the figures thus far. A number of alternative constructions will be described herein below. For all these electrodes structure, however, it will sometimes be desirable to provide a penetration limit so that the electrodes may be advanced into the marginal tissue at a desired depth, typically within the ranges set forth above. As shown in FIGS. 6 and 7, an exemplary electrode 36 having a tissue-penetrating tip 37 includes a collar 38 spaced at a distance d from tissue-penetrating tip 37. The collar 38 will usually be collapsible, for example being formed from a flexible or elastomeric material, so that it may be collapsed within a deployment channel 40 within an applicator head, for example applicator head 26 as shown in FIG. 4. When the needle 36 is advanced from the applicator head 26, as shown in FIG. 8, the collars 38 will deploy radially outwardly and will serve to limit the penetration of the distal portion of the electrode into the tissue T. When the applicator head 26 is within a body cavity BC, the electrodes 36 may be advanced by different distances from the surface of the applicator head 26, but the distal penetration of each electrode 36 will limited to a similar or equal depth as al other electrode tips. Thus, even though the applicator head has not fully conformed to the inner surface of the body cavity BC, the electrodes may be advanced by different distances from the exterior surface of the applicator head yet still achieve equal penetration depths. Such embodiments are particularly useful when treating irregularly shaped body cavities. The engagement of the collar 38 against the inner wall of the body cavity BC is best illustrated in FIG. 8A where the penetration depth into the tissue margin TM is shown.

Figure 8C:
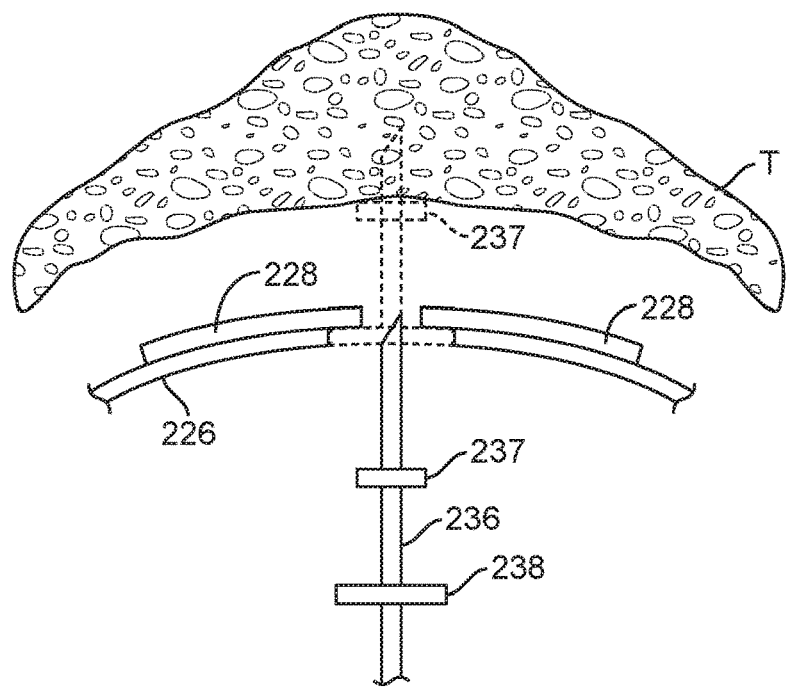
FIG. 8C illustrates a distal end of a single electrode having both a penetration-limiting collar and an electrically conductive disc or flange element disposed to engage a surface electrode on the applicator head.

FIG. 8B illustrates an electrode 136 having an electrically conductive disc or flange 137 spaced proximally from a tissue-penetrating tip. The disc or flange 137, when advanced radially outwardly, both limits the travel of the electrode and engages an inner side of surface electrode 138 to provide a conductive path to that electrode so that energizing the electrode will simultaneously energize the surface electrode into tissue T. FIG. 8C illustrates an electrode 236 having both a collar 238 spaced proximally from a tissue-penetrating tip and electrically conductive disc or flange 237 spaced between the tissue-penetrating tip and the disc 237. The disc or flange 237, when advanced radially outwardly, both limits the travel of the electrode and engages an inner side of surface electrode 238 to provide a conductive path to that electrode so that energizing the electrode will simultaneously energize the surface electrode. The collar 237 further limit the penetration of the electrode into the tissue T.

Figure 9:
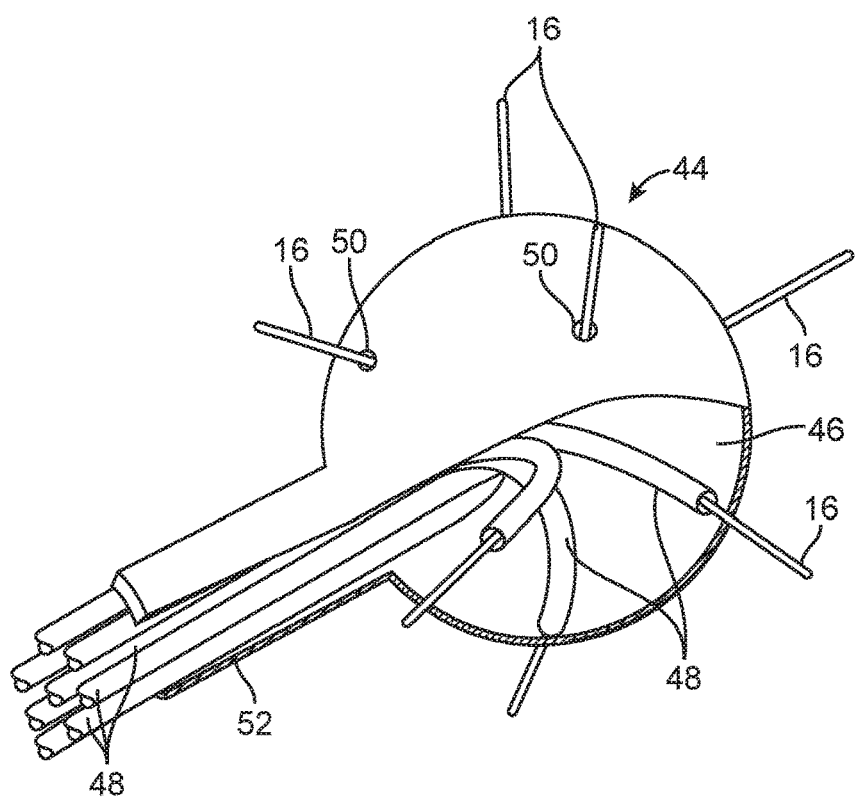
FIG. 9 illustrates a hollow core or open interior embodiment of an applicator head having a plurality of curved tubes for deflecting individual electrodes and optionally delivering irrigation or other fluids in accordance with the principles of the present invention.
Figure 10:
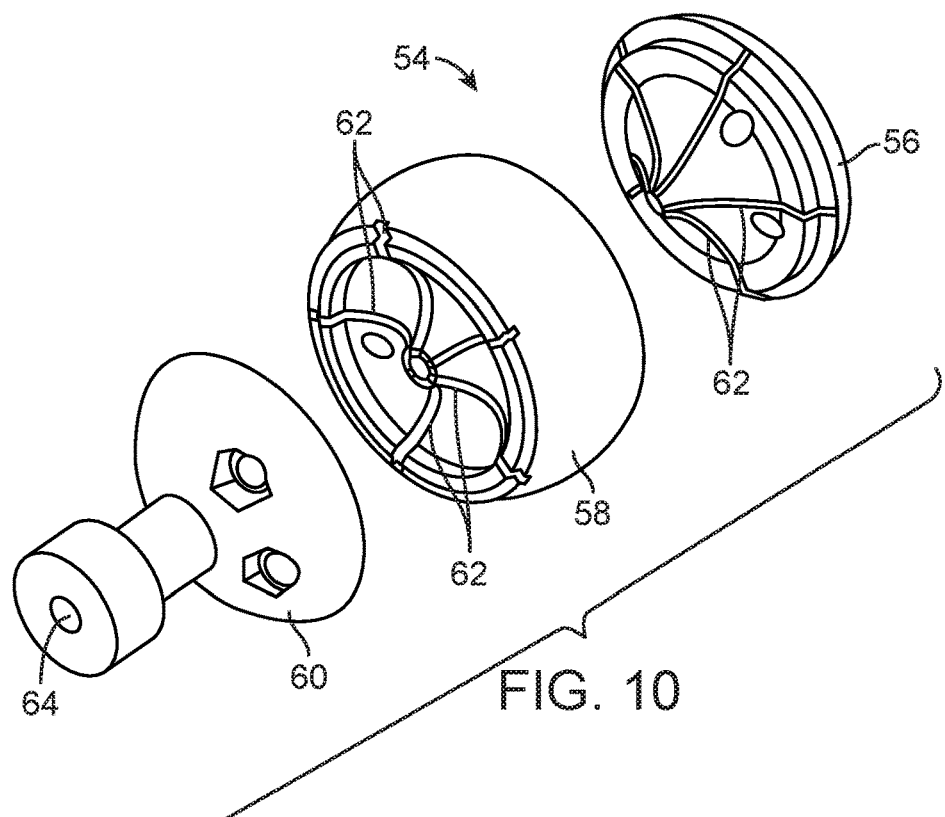
FIGS. 10 and 11 illustrate alternative constructions of applicator heads in accordance with the principles of the present invention having solid cores with electrode-deflecting channels formed therein. The channels can also be configured for irrigation.

Referring now to FIG. 9, a specific example of an applicator head 44 having an open interior 46 with a plurality of electrode-electrode deployment tubes 48 therein is illustrated. The tubes 48 are shaped to receive and deflect individual electrodes 16 so that the deployment directions of each electrodes 16 may be individually selected and, in particular, so that the electrodes may be deployed in an omnidirectional pattern, as described above. Thus, some of the individual electrodes 16 will be directed distally from the applicator head 44 while others will be everted and directed proximally from the application head. Usually, the tubes 48 will extend through at least a portion of the length of the shaft 52, and a mechanism in the shaft (not shown) will be provided for advancing the electrodes through each of these tubes 48. An applicator head 54 having a further alternative construction is illustrated in FIG. 10. The applicator head 54 has a generally solid body which includes a distal segment 56, a middle segment 58 and a proximal segment 60. Adjacent surfaces of the segments will have channels 62 formed therein for receiving and deflecting individual electrodes (not shown) in distally and proximally oriented patterns. The channels 62 will be contiguous with a central passage 64 which will receive the individual electrodes that are advanced and retracted using any of the shaft or handle mechanisms described herein.

Figure 11:
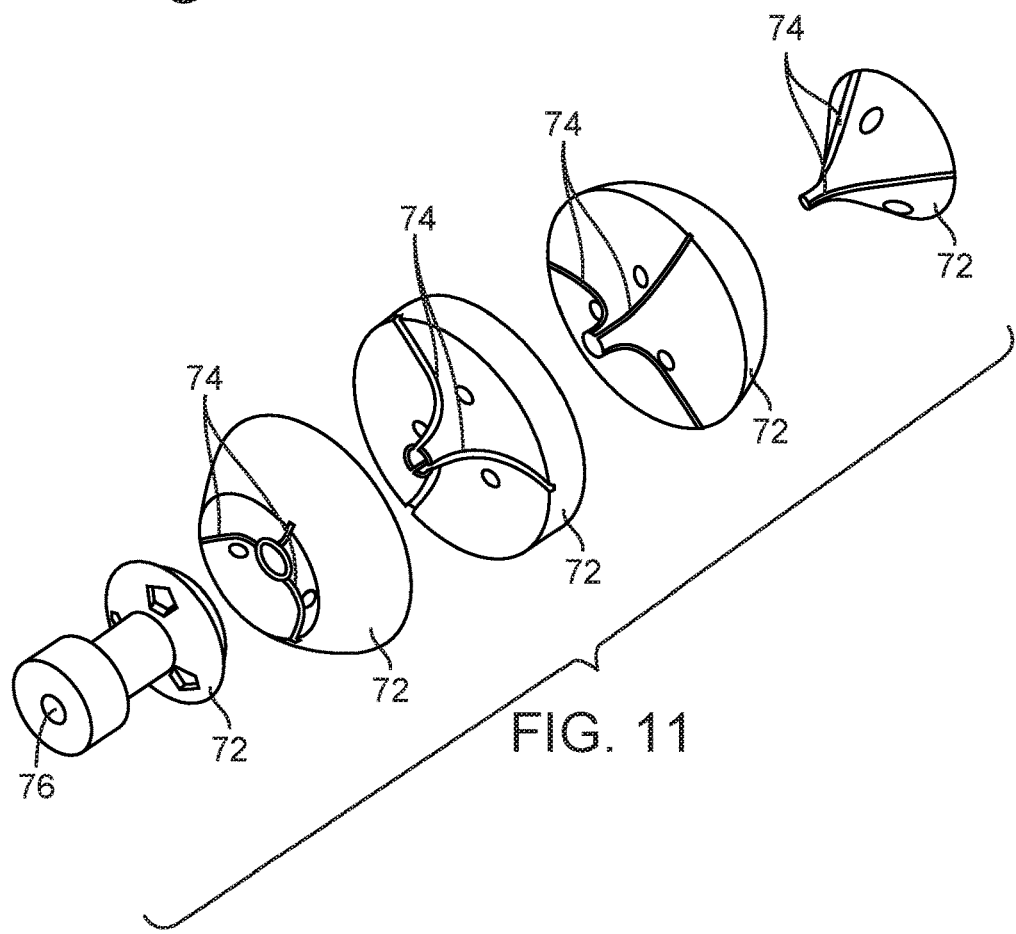

FIG. 11 illustrates a similar solid core applicator head 70 which includes five individual segments 72, each having channels 74 formed therein for deploying individual electrodes (not shown). The channels 74 are contiguous with a central passage 76 to allow the electrodes to be advanced and retracted. The use of additional segments allows an increased number of electrodes with improved axial distribution of the individual electrodes compared with the use of three segments as shown in FIG. 10.

Figure 12:
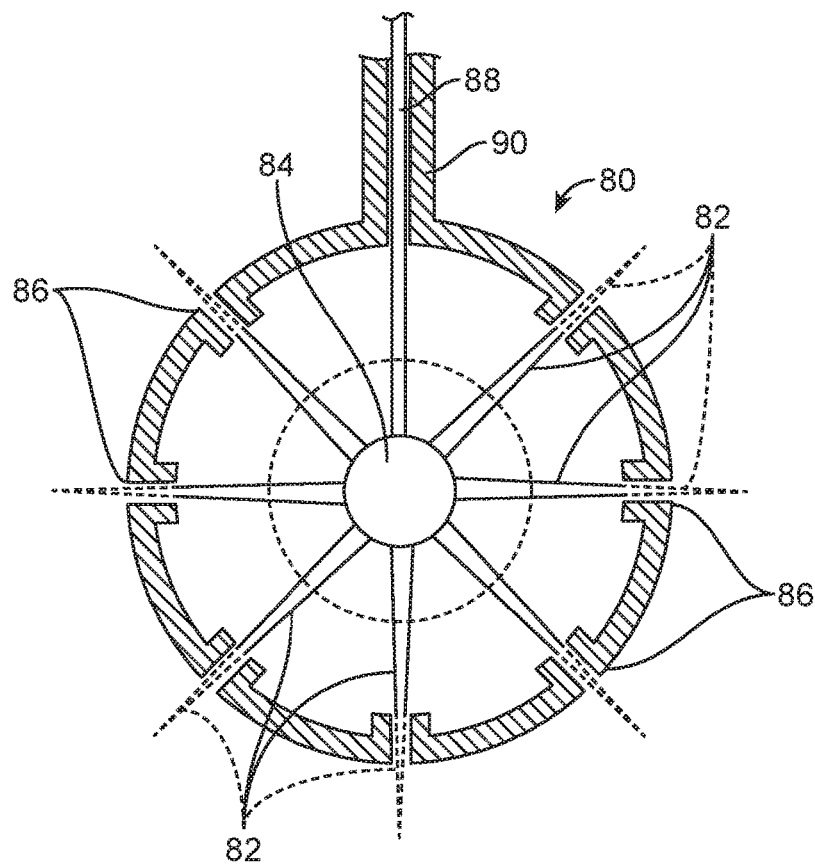
FIG. 12 illustrates a further embodiment of an applicator head constructed in accordance with the principles of the present invention which utilizes an expandable support for deploying a plurality of relatively rigid electrodes in a radially outward direction.

Applicator head 80 illustrated in FIG. 12 comprises an alternative mechanism for advancing electrodes from the applicator head. Electrodes 82 are mounted on an expandable support 84, typically and inflatable support such as a balloon which may be inflated through inflation line 88. The electrodes 82 are usually short, rigid electrodes aligned with ports 86 formed through a shell of the applicator head 80. The interior of the applicator head is generally open and free from structure so that the expandable support 84 may be expanded from a contracted configuration, as shown in full line, to an expanded configuration, shown in broken line. As the support expands, the individual electrodes 82 are advanced through the ports 86 to penetrate the surrounding tissue.

Figure 13:
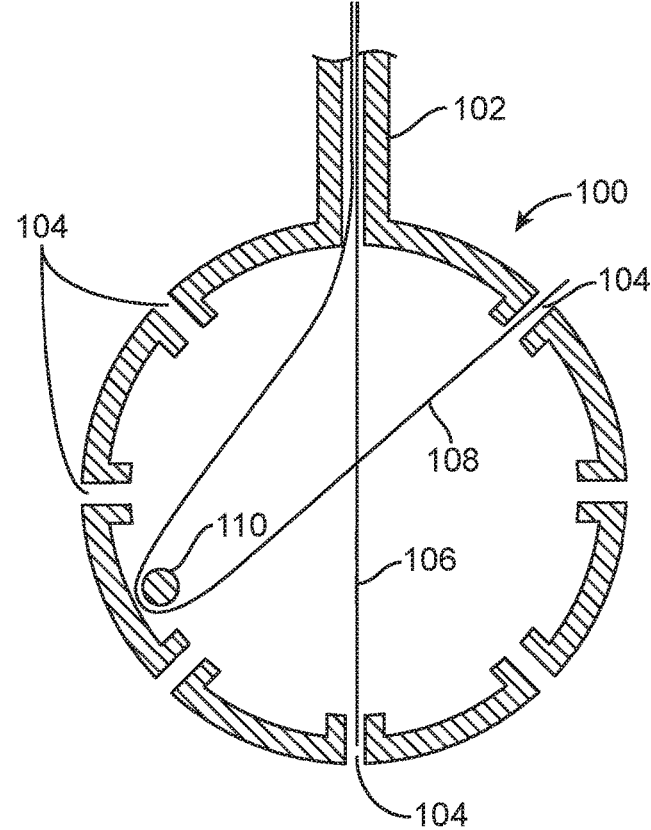
FIG. 13 illustrates a still further embodiment of an applicator head constructed in accordance with the principles of the present invention which deploys a plurality of elongate straight electrodes, some of which are routed around guide posts in order to effect a reversal of direction.

A still further electrode advancement mechanism is shown in FIG. 13 where applicator head 100 comprises a shell having a plurality of ports 104 formed therein. Elongate, flexible electrodes 106 are advanced through a neck or shaft 102 of the probe. Only two individual electrodes 106 are illustrated, but it will be appreciated that typically at least one electrode will be provided to be advanced through each of the illustrated ports. Usually, additional ports will be provided, but only those ports shown on the sectional plane of the drawing are illustrated for convenience. Many of the individual electrodes 106 may be advanced through an associated port without the need to provide for additional guidance. Others of the electrodes, however, will need to be everted so that they may be deployed in a proximal direction. In such cases, the electrodes 106 may be advanced around a guide post 110 which can at least partially reverse the direction of travel of the electrode.

Figure 14:
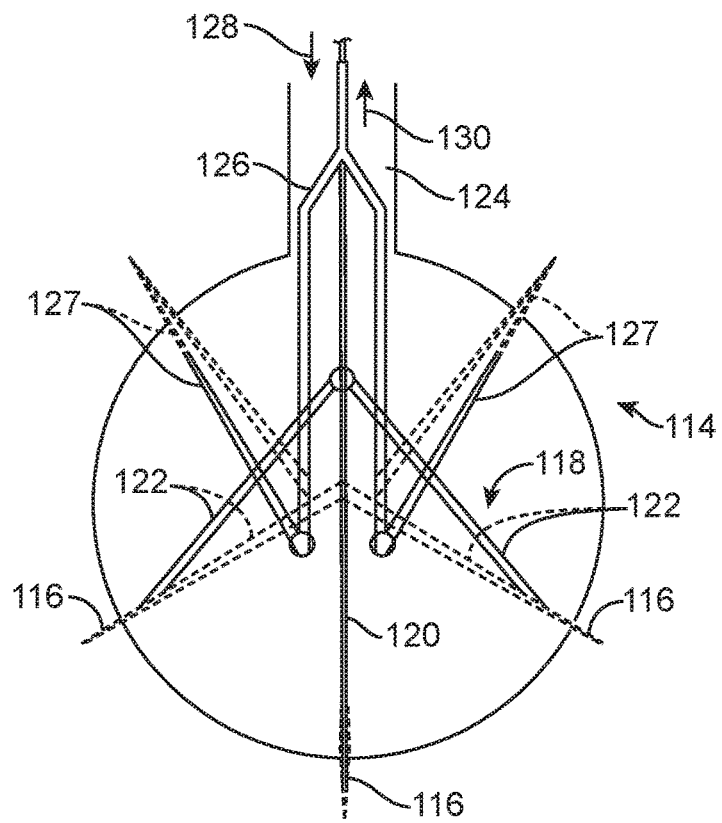
FIG. 14 illustrates yet another embodiment of the applicator head of the present invention which employs push- and pull-mechanisms for deploying the electrodes in distal and proximal directions, respectively.

Yet another electrode deployment mechanism is illustrated in FIG. 14 where applicator head 114 has an outer shell with a plurality of ports 116 formed therein. Electrodes 120 and 122 which are advanced in a generally distal direction are connected in "push" assembly 118 so that they may be advanced in the direction of arrow 128 by pushing on a proximal portion of the central electrode 120. Other electrodes 127, in contrast, are intended to be deployed in a proximal direction and will be incorporated into a "pull" assembly 124 including a yoke 126 which may be pulled in the direction of arrow 130 in order to deploy these electrodes. All the electrodes may be simultaneously deployed by pushing and pulling on the rods attached to these assemblies simultaneously as shown by arrows 128 and 130.

Figure 15:
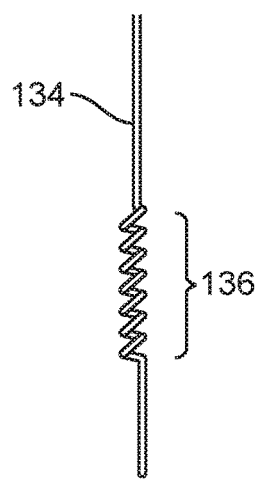
FIG. 15 illustrates an electrode having a spring-like region to enhance bendability.
Figure 16:
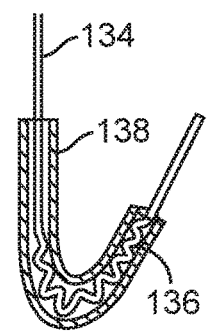
FIG. 16 illustrates the electrode of FIG. 15 being deployed through a tight curve in a deployment tube.

As some of the electrodes in the applicator head embodiments of the present invention will be subjected to very tight turns, typically for those being deployed proximally from the applicator head, it can sometimes be useful to provide elastic regions 136 in electrodes 134, as illustrated in FIG. 15. The elastic regions may be a short coiled section or may have other modifications in order to decrease pending stiffness. For example, the surfaces of the electrodes could have small notches or wedges formed therein to allow easier deformation. As shown in FIG. 16, the elastic regions 136 may be disposed so that they lie at a location where the tightest bend will be found, for example in a deployment tube 138.

Figure 17:
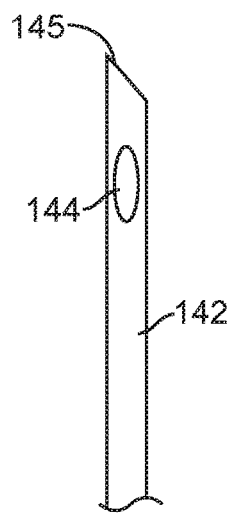
FIG. 17 shows an electrode having a sensor thereon.

Referring now to FIG. 17, individual electrodes 142 may include one or more sensors 44 formed near their distal tips 145. Sensors can be configured to measure temperature, impedance, or the like. In some instances the sensors may be configured to determined depths of penetration, for example using a capacitance measurement protocol.

Figure 18:
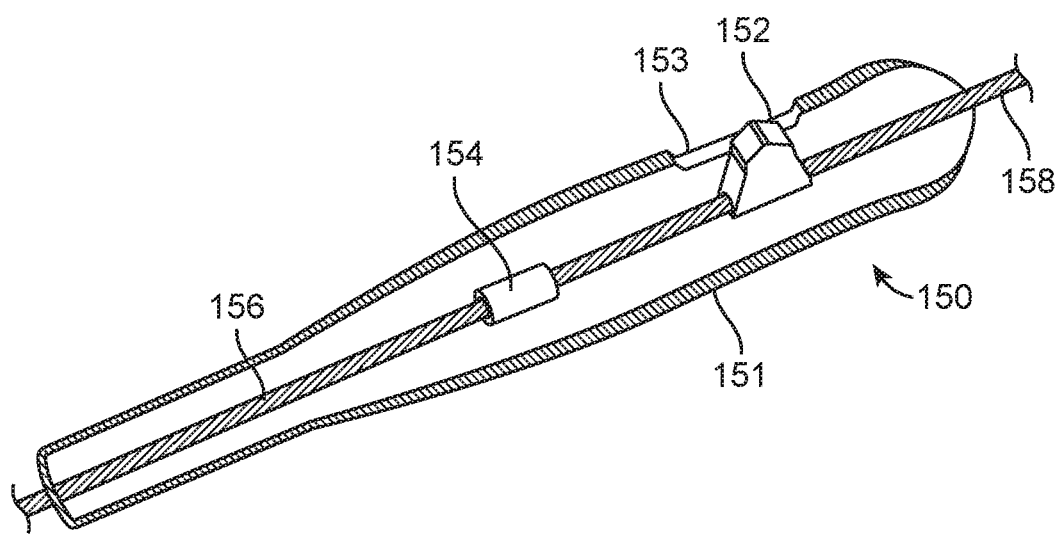
FIG. 18 illustrates an exemplary handle for manual manipulation of the probe of the present invention, where the handle has a single deployment slide which is coupled to the plurality of electrodes.

Referring now to FIG. 18, an exemplary handle 150 which can provide all or a portion of a shaft structure is illustrated. Then handle 150 comprises a shell or enclosure 151 having an open interior and a slot 153. Slider 152 is received within the slot so that it may be manually advanced and retracted by a user. Slider 152 is connected to a cable 156 or other element which is connected to the plurality of electrodes in the probe, where the electrodes can have many of the embodiments described previously. A displacement sensor 154 is provided within the interior of the handle 150 and measures the distal advancement and proximal retraction of the cable as the slider 152 is advanced and retracted. In this way, the net displacement of the electrodes and their penetration into the tissue can be monitored.

Figure 19:
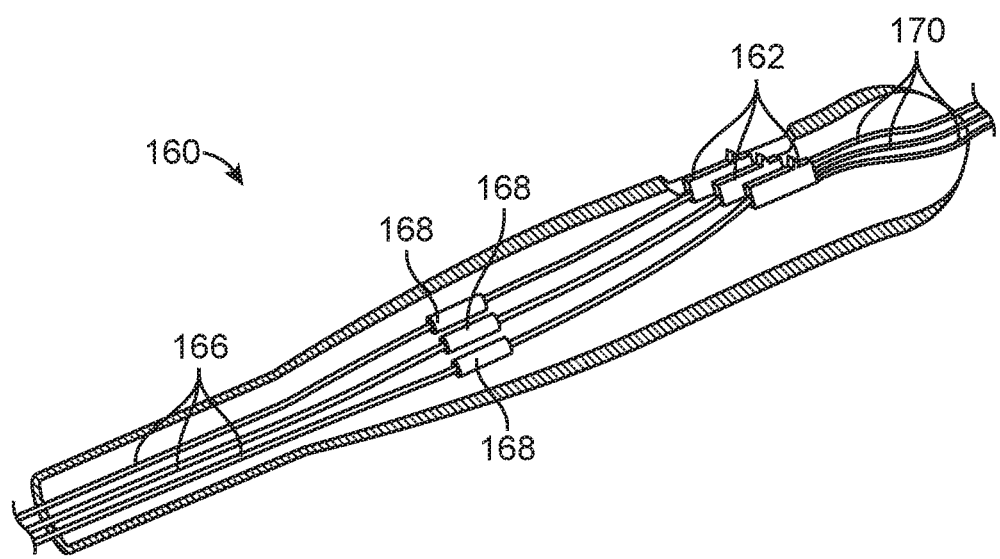
FIG. 19 illustrates an alternative handle embodiment having a plurality of slides for deploying individual ones of the plurality of electrodes in the probe.

The construction of an alternative handle 160 is illustrated in FIG. 19. The principal difference between handle 160 and handle 150 is that a plurality of sliders 162 is provided in handle 160. Each slider 162 is attached to an individual electrode 166 and a plurality of individual displacement sensors 168 are provided, one for each of the sliders and electrode pairs. In this way, each individual electrode can be advanced by a different distance and the handle can monitor the displacement distances individually. Each of the individual electrodes 166 will be connected to the radio frequency power supply by individual connection leads 170. Handle 150 included a single connection lead 158.

Referring now to FIGS. 20-22, exemplary multi-polar electrodes 174 may include individual electrically conductive and electrically insulating regions. As illustrated, the multi-polar electrodes 174 include a top conductor region 176 and middle conductor region 178. The conductor regions 176 and 178 are separated by an insulating region 180. A further insulating region 180 may be provided between the middle conductor region 178 and a base region 182. The base region 182 will usually be a portion of the applicator head so that the electrode 174 will be able to pass the through the base. The electrically conductive regions 176 and 178 as well as the base region 182 may be powered at a common polarity or with different polarities. As shown in FIG. 21, the top conductor region 176 may have a positive polarity while the middle and base may have negative polarities. Other combinations will be available. Shown in FIG. 22, assuming that each individual electrode 174 is powered at a common polarity, the adjacent electrodes may themselves be powered at difference polarities in order to achieve a bipolar configuration.

Figure 23:
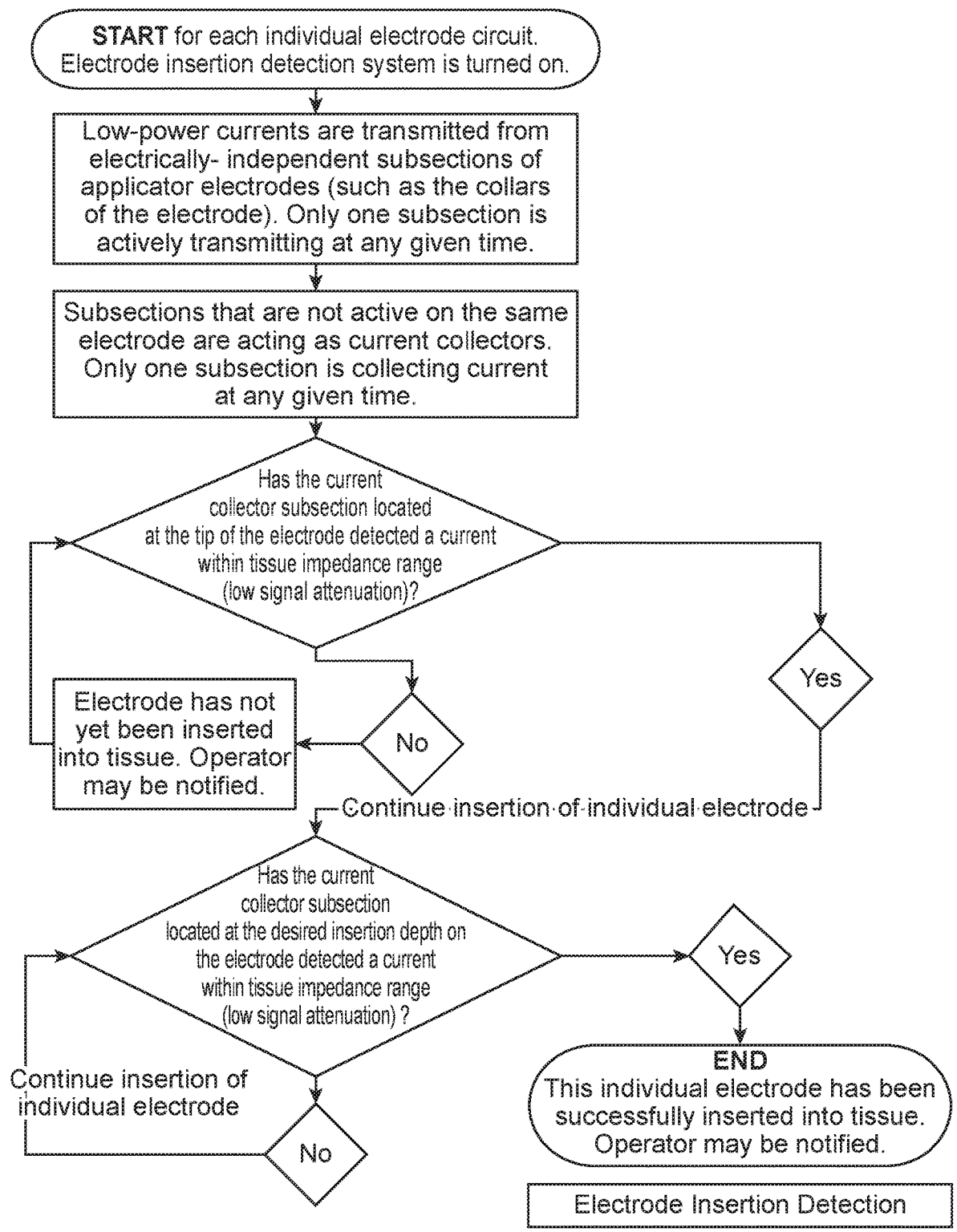
FIG. 23 is a flowchart illustrating an exemplary protocol for electrode insertion detection.

Referring now to FIGS. 23-27, the probes of the present invention will typically be powered by radiofrequency power supplies having microprocessors which may be configured to provide a numbers specific operational protocols. For example, as shown in FIG. 23, the power supplies may have protocols which detect when electrodes having collars, as shown in FIGS. 6-8, are fully inserted. The flowcharts are self-explanatory. Briefly, these protocols rely on using electrodes having different regions of electrical conductivity, where those regions are electrically isolated. These regions are subsections which are energized with low-power current, and the various regions on individual electrodes may be monitored to see when that region or subsection has entered tissue in order to detect a flow of power which is present only when that subsection is within tissue. When the electrode region or subsection at the desired depth is detected to have been inserted into tissue, the system can confirm that the proper depth of penetration has been achieved.

Figure 24:
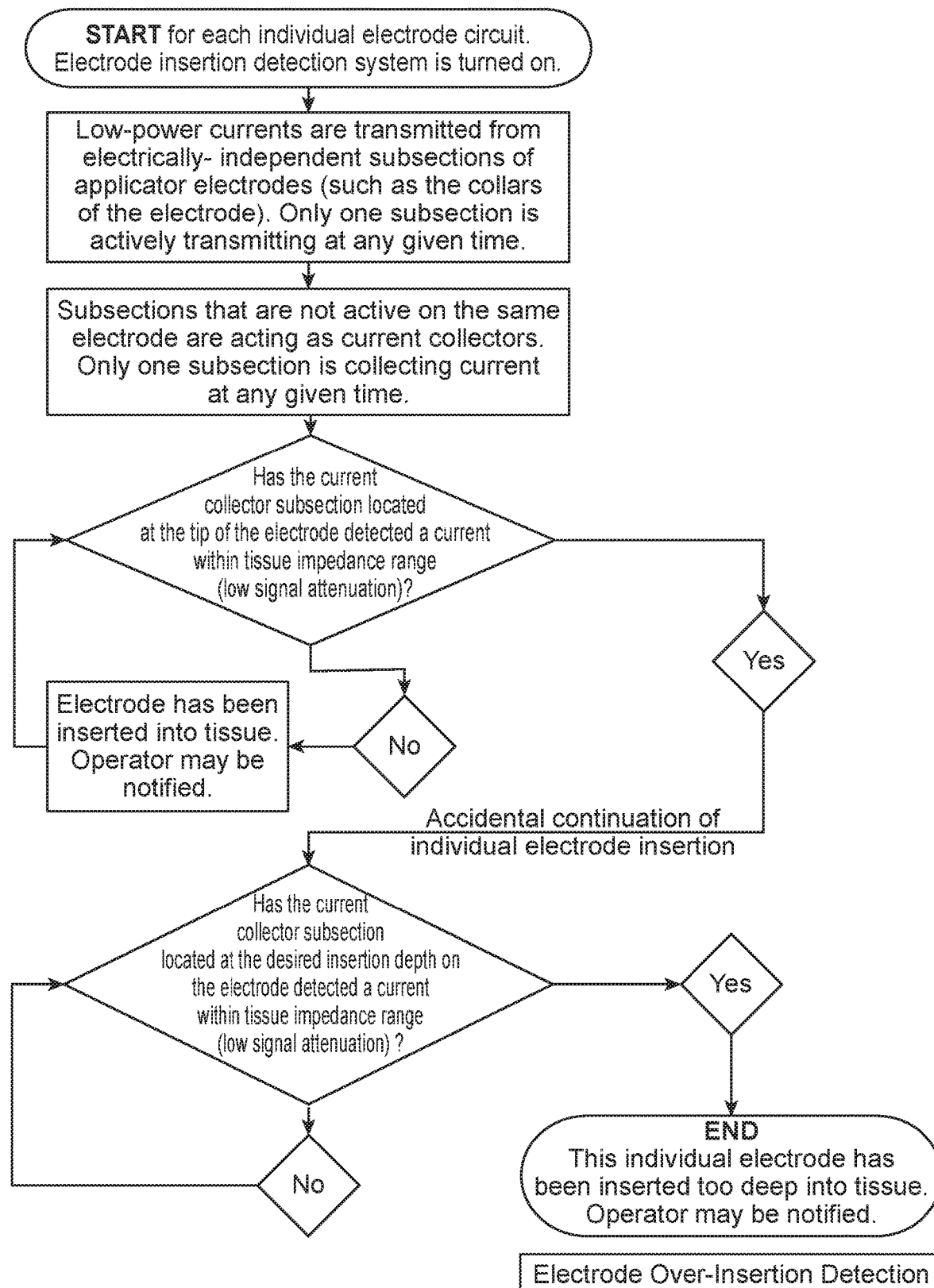
FIG. 24 is a flowchart illustrating an exemplary protocol for determining electrode over-insertion.

Referring now to FIG. 24, a protocol for detecting on the electrodes have been over-inserted is set forth. Again, the protocols are self-explanatory but generally rely on using electrodes having multiple, isolated electrically active regions so that a low power signal passing through those regions will be detected by the power supply when that region has entered tissue. If a region which is beyond the desired penetration depth enters the tissue, the system will detect that the electrode has been over-penetrated into the tissue.

FIG. 25 illustrates a specific protocol for operating the power supplies to deliver energy through the probes of the present invention. Using electrodes that contain sensors, such as illustrated in FIG. 17, allows temperature and other data to be collected. In addition, the electrically-isolated regions of a specific electrode can be used to transmit a low-power signal and determine the conductivity of the tissue through which the signal has passed. The aggregation of the measured data is used in the protocol described in FIG. 25 to determine when an ablation protocol has been completed.

FIG. 26 illustrates a protocol for ablation mapping where a geometric representation of the current state of the ablation volume is created. The same data as collected in the protocol in FIG. 25 are mapped to the geometric location of the sensors or regions of specific electrodes, thus linking the ablation index to a specific region of tissue. The series of these ablation index and tissue region pairs form a three-dimensional map of the current three-dimensional ablation volume, relative to the orientation of the applicator shaft. This allows either an external microprocessor-based system to automatically control the polarities and potentials on the different electrodes and their regions or for the user to manually adjust the electrical supply through the device to effect the desired ablation shape and volume.

FIG. 27 illustrates a protocol for a typical ablation procedure, which includes shaping of the cavity to prepare the cavity for consistent, optimal ablation. By following the steps in the protocol, the cavity can be matched to the shape of the applicator head.

What is claimed is:

1. A probe for ablating tissue surrounding a body cavity, said probe comprising:
   a shaft having a distal end;
   an applicator head comprising a shell having an interior volume and a spherical outer surface which is fixedly configured to occupy a volume of the body cavity, said shell having a plurality of ports distributed over the outer surface;
   a plurality of electrodes disposed within the interior volume of the applicator head, wherein said electrodes have distal portions which extend through the ports beyond the outer surface of the applicator head;
   wherein at least some of the plurality of ports are distributed over a distal hemispherical portion of the spherical outer surface and at least some of the plurality of ports are distributed over a proximal hemispherical portion of the spherical outer surface.

2. A probe as in claim 1, wherein the shaft is configured as a handle adapted for manual manipulation.

3. A probe as in claim 1, wherein the applicator head has an open interior, further comprising a radially expandable support which reciprocatably carries the plurality of electrodes.

4. A probe as in claim 3, wherein the radially expandable support comprises an expandable bladder.

5. A probe as in claim 1, wherein the applicator head has an open interior and wherein at least some of the individual electrodes are configured to evert around a guide post within the open interior.

6. A probe as in claim 1, wherein the electrodes are configured to advance from the applicator head in an omni-directional pattern.

7. A probe as in claim 6, wherein the omnidirectional pattern comprises a plurality of paths which radiate radically outwardly from a virtual center point within the applicator head.

8. A probe as in claim 7, wherein the plurality of paths are distributed substantially evenly in a space surrounding an exterior surface of the applicator head.

9. A probe as in claim 6, wherein the electrodes are configured to advance from the applicator head so that at least some of the electrodes advance from the applicator head in a distally diverging pattern and at least some of the electrodes advance from the applicator head in a proximally diverging pattern.

10. A probe as in claim 9, wherein the electrodes are configured to be advanced in parallel in a distal direction through the shaft and to be deflected within the applicator head so that some distally diverging electrodes continue to advance distally while said proximally diverging electrodes are everted at an angle between 90 degree and 180 degree.

11. A probe as in claim 1, wherein the plurality of electrodes comprises at least six electrodes.

12. A probe as in claim 1, wherein at least some of the electrodes comprise a superelastic material.

13. A probe as in claim 1, wherein at least some of the electrodes have two or more isolated electrically conductive regions.

14. A probe as in claim 1, wherein the plurality of electrodes comprise at least a first polarity group and a second polarity group.

15. A probe as in claim 1, further comprising one or more electrodes on the shaft.

16. A probe as in claim 1, further comprising one or more electrodes disposed on the outer surface of the applicator head.

17. A probe as in claim 16 wherein the one or more electrodes are affixed to the outer surface of the applicator head.

18. A probe as in claim 1, wherein at least a portion of the applicator head comprises an electrically non-conductive material.

19. A probe as in claim 1, wherein at least a portion of the applicator head comprises an electrically conductive material.

20. A probe as in claim 17, wherein at least some of the electrodes and surface electrode(s) are configured to be connected to a power supply in isolation from others of the electrodes and surface electrode(s) so that electrical currents can be selectively delivered to at least some of the electrodes and surface electrode(s) to allow customization of the ablation shape.

21. A probe as in claim 1, wherein the plurality of ports distributed evenly over the outer spherical surface.

* * * * *